United States Patent [19]
Silver

[11] Patent Number: 5,476,490
[45] Date of Patent: Dec. 19, 1995

[54] HEATING PAD

[75] Inventor: Brian Silver, Cary, Ill.

[73] Assignee: Medela, Inc., McHenry, Ill.

[21] Appl. No.: 241,160

[22] Filed: May 10, 1994

[51] Int. Cl.⁶ ..................................................... A67F 7/00
[52] U.S. Cl. .......................................... 607/108; 128/890
[58] Field of Search .................................. 128/890, 846; 607/108; 602/14

[56] References Cited

U.S. PATENT DOCUMENTS

| | | | |
|---|---|---|---|
| 986,738 | 3/1911 | Milligan. | |
| 2,298,361 | 10/1942 | Freund | 607/108 |
| 4,077,390 | 3/1978 | Stanley | 126/263 |
| 4,263,912 | 4/1981 | Adams | 128/281 |
| 4,323,067 | 4/1982 | Adams | 128/281 |
| 4,572,158 | 2/1986 | Fiedler | 126/263 |
| 4,740,196 | 4/1988 | Powell | 604/75 |
| 4,872,442 | 10/1989 | Manker | 126/263 |
| 4,880,953 | 11/1989 | Manker | 219/10.55 |
| 5,050,595 | 9/1991 | Krafft | 607/108 |
| 5,058,563 | 10/1991 | Manker | 126/263 |
| 5,074,300 | 12/1991 | Murphy | 607/108 |
| 5,230,335 | 7/1993 | Johnson | 607/108 |
| 5,235,974 | 8/1993 | Miller | 607/108 |
| 5,304,215 | 4/1994 | MacWhinnie | 602/14 |

FOREIGN PATENT DOCUMENTS

| | | |
|---|---|---|
| 2807646 | 8/1978 | Germany. |
| 533493 | 2/1941 | United Kingdom. |
| 660283 | 11/1951 | United Kingdom. |
| 2155792 | 10/1985 | United Kingdom. |

OTHER PUBLICATIONS

Medela, Inc., "Engorgement Therapy Bra" Literature re: Heat Solution, WarmGel Pack and Prism Infant Heel Warmer.

*Primary Examiner*—Michael A. Brown
*Attorney, Agent, or Firm*—Willian Brinks Hofer Gilson & Lione

[57] ABSTRACT

A heating pad is disclosed. The heating pad is essentially "C-shaped" and is filled with a chemical composition. When activated by the triggering device, the chemical composition undergoes a reversible exothermic reaction and generates heat that warms the breast or other body part with which it is in contact. Because of its shape, the heating pad fits comfortably around the human female breast and efficiently transfers heat to the breast when activated. Also disclosed is an embodiment where the heating pad is connected to a breast pump so that the heating pad warms the breast while the breast pump is being used.

16 Claims, 3 Drawing Sheets

HEATING PAD

FIELD OF THE INVENTION

This invention relates to single use or reusable heating pads. These heating pads are especially shaped so as to comfortably and efficiently fit on a human female breast. Their shape also makes them particularly suited to provide heat to the knees, face and other areas of the body. These heating pads contain a chemical composition that develops heat when activated by a triggering device, wherein the chemical composition can preferably be reused for further applications of heat after being recharged.

In another embodiment, this invention also relates to a combination of a breast pump with a single-use or reusable heating pad for warming the human female breast. This combination allows the woman to continue warming her breast while simultaneously using the breast pump to express her milk.

BACKGROUND OF THE INVENTION

Heat packs of various types have long been used in the medical field and by sportsmen for the purpose of applying heat to localized areas of the body to alleviate stiffness or minimize tissue damage due to freezing, for example.

Heat packs employing hot water or electrically-generated heat suffer from certain disadvantages in convenience of use. These disadvantages have been overcome by the use of super-saturated salt solutions inside sealed containers that are activated to crystallize and thereby generate heat. The temperature achieved by such devices can be controlled based upon the type of salt used and its concentration. When the crystallization is complete, the salt is returned to its super-saturated condition by heating the sealed container in hot water, by microwave radiation, or by other heat sources.

The activation of super-saturated salt heating pads is carried out by the flexing of a metal disk that contains slits through its thickness. The slits may start at the edge of the metal disk and terminate in its interior, or they may be entirely within the interior of the disk. It has been theorized that these metal disks initiate crystallization by presenting at the termini of the slits new metal surfaces that are created by the flexing of the metal disk. In some metal disks, the disks are roughened after the slits are formed, this roughening producing minute nodules of metal on the disk. It is theorized that these roughened metal disks release some of these nodules when the disk is flexed, and that the nodules are responsible for initiating crystallization. Further information about these disks and the super-saturated salt solutions that they activate is available from U.S. Pat. Nos. 4,077,390 to Stanley et al., 4,572,158 to Fiedler, and 4,872,442, 4,880,953, and 5,058,563 all to Manker, the entire disclosures of which are hereby incorporated by reference.

The application of heat to the human female breast prior to and during expression results in improved comfort to the woman. It also may enhance letdown, relieve engorgement and soften the areola. Additionally, heat increases the blood flow to the tissue, thereby improving the woman's comfort and the activity of the breast tissues. Finally, the comfortable feelings derived from the application of heat to the breast tends to exert a calming effect and relieve stress in the woman, both of which increase the chances of successfully feeding of the infant or the expression of milk through use of a breast pump or hand expression.

SUMMARY OF THE INVENTION

This invention is a single use or re-usable heating pad for warming a breast or other parts of the body. It consists of a hollow, flattened, interrupted toroidal container that is filled with a chemical composition. The chemical composition can undergo an exothermic reaction when triggered, and for the re-usable heating pad may be recharged after completion of the exothermic reaction so as to be able to undergo successive exothermic reactions.

Another embodiment of this invention is the method for making a heating pad that comprises the steps of providing a C-shaped front piece comprising a water-proof material, heat sealing a C-shaped back piece comprising a water-proof material to said front piece so as to form a water-proof cavity, die-cutting the edges of the heat-sealed front and back pieces, placing a chemical composition that is capable of undergoing an exothermic reaction inside said cavity, and placing a triggering device that instigates said exothermic reaction inside said cavity.

The heating pad described herein provides an improvement over previous methods of warming the breasts, and over previous heating pads for generating heat from an exothermic reaction. Although heating pads that generate heat from an exothermic reaction are known in the art, none has before been made that is shaped to specifically fit over the human female breast and to comfortably apply heat thereto.

DETAILED DESCRIPTION OF THE PRESENTLY PREFERRED EMBODIMENTS

Figure 1:
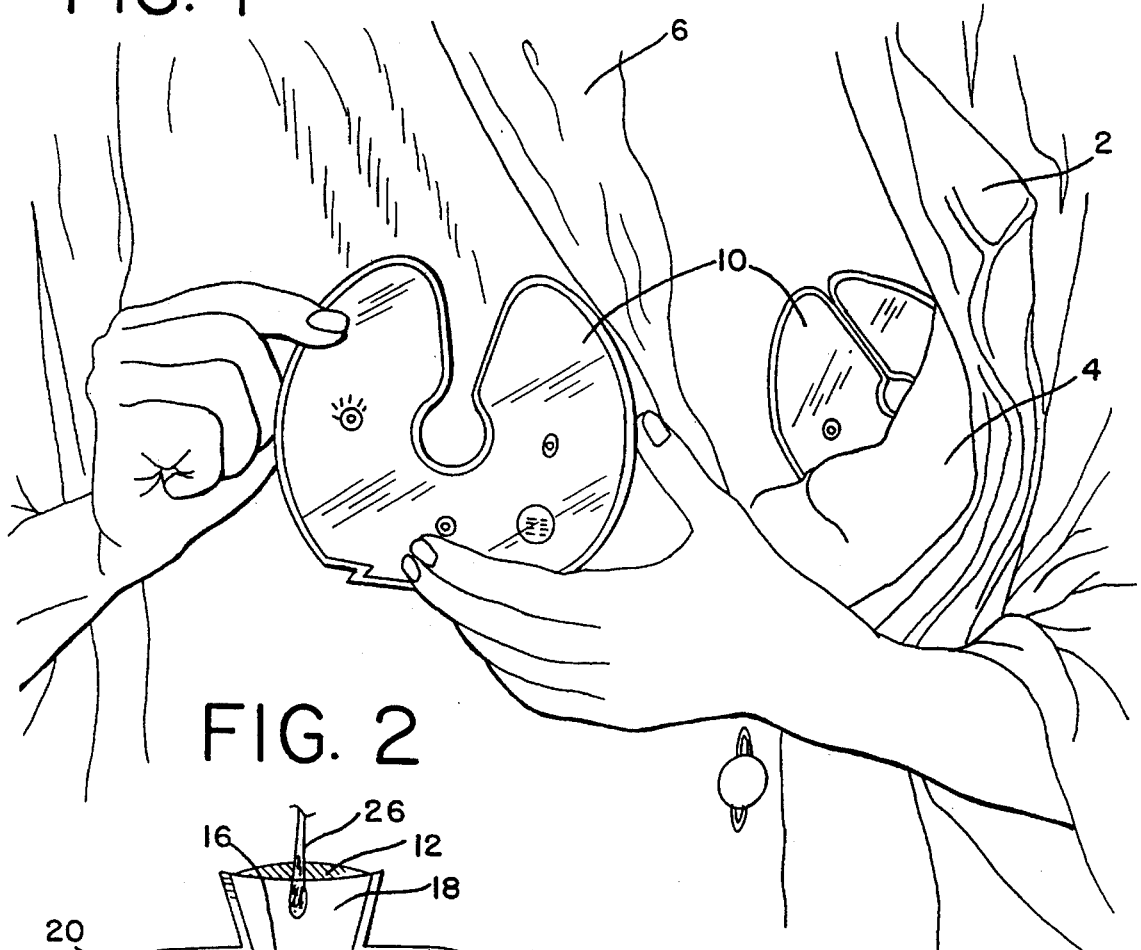
FIG. 1 is a perspective view of a woman using an embodiment of the invention.

With reference to FIG. 1, shown are the preferred methods for applying a heating pad 10 to a breast 2. On the left, FIG. 1 shows the user holding the heating pad 10 against the breast 2 on the outside of her blouse 6. On the right a preferred alternative is shown, wherein the user has placed the heating pad 10 inside her brassiere 4 and directly against the skin of her breast 2.

Figure 2:
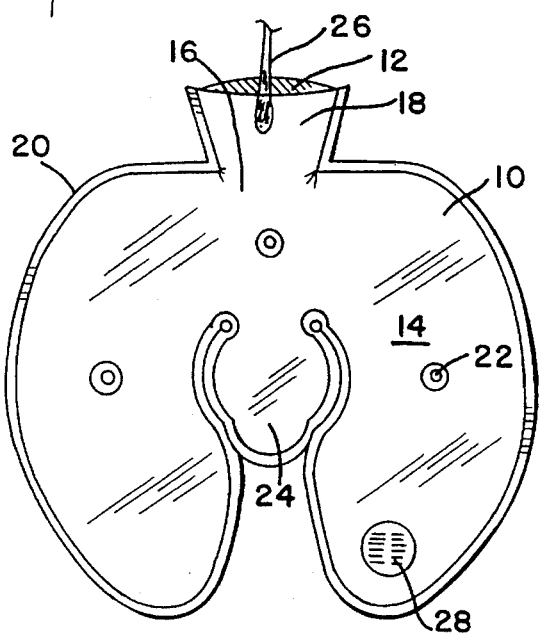
FIG. 2 is a top plan view of an embodiment of the invention, including the fill spout.

FIG. 2 shows the heating pad 10 after the external parts have been assembled, and while the internal contents are being placed inside. At this point the heating pad 10 includes a front piece 12 and a back piece 14 (see FIG. 7) that have been connected along their periphery while leaving an opening into the cavity 16 that is formed between them. This opening is seen in the fill spout 18 in FIG. 2.

The front piece 12 and the back piece 14 may be formed from any suitable material that is flexible, water-proof, is not affected by the contents of the heating pad 10, and which withstands the temperature extremes to which the heating pad 10 is subject. The pieces are preferably composed of plastic, in particular vinyl, nylon, polyester or urethane. Most preferably they are composed of vinyl plastic. A thickness of 22 gauge is the most preferred thickness of plastic, although other thicknesses can clearly be used to meet the objects of the invention. It is also preferable for at least a portion of the front piece 12 or back piece 14 to be transparent. This aids in locating the triggering device 28, and in the reusable version that utilizes a super-saturated salt solution, it aids in determining that all of the salt crystals are dissolved when heating the heating pad 10 to recharge it.

As shown in the figures, the front piece 12 and the back piece 14 are essentially "C-shaped." This shape includes an outer circular circumference, and inner circular circumference, and an interruption of the circles by a gap in the pieces. In a preferred embodiment, a portion of the sealed edge 20, opposite the gap, is flattened. This flattened portion 21 of the edge allows the heating pad 10 to fit better when placed inside the brassiere 4 as shown in FIG. 1. In the embodiment shown in FIG. 2, the inner circle of the "C" is essentially filled with the material that forms the nipple cover 24. The finished product maintains this C-shaped appearance, and it therefore can be manipulated so that when the ends of the "C" are brought together, a conically shaped heating pad that is properly shaped to fit over the human female breast is created. However, depending upon the size and shape of the breast 2, the heating pad 10 may fit comfortably without bringing together the ends of the "C."

The connection between the front piece 12 and the back piece 14 is shown as the sealed edge 20. The sealed edge can be created by heat sealing, ultrasonic welding, radio-frequency welding, or other ways known in the art. Also, the front piece 12 and back piece 14 may be produced as a single piece through blow-molding, rotation molding, or other means known in the art. In a most preferred embodiment, the edge 20 is heat-sealed and then die-cut so as to present a smooth edge that is less likely to discomfort the user of the heating pad 10.

When the front piece 12 and the back piece 14 are sealed together, it is also advantageous to form three point seals 22 between the pieces by the same sealing method. These give added stability to the heating pad 10 and help to keep it in its proper flattened shape, without unduly infringing upon its flexibility. By maintaining the shape of the heating pad 10, the chemical composition 26 is kept essentially evenly distributed without creating bulges that would inhibit the efficient use of the heating pad 10. This also minimizes the amount of the chemical composition 26 needed to fill the heating pad 10. Of course, more or fewer point seals may be used than the three shown.

Also shown in FIG. 2 is the nipple cover 24. The nipple cover 24 is shown as contiguous with the front piece 12 and the back piece 14. The interior of the nipple cover 24 is also contiguous with the cavity 16 formed when the pieces are sealed. It is also a flexible part that may remain in the position shown if the user wishes to cover and warm her nipple, or it may be tilted away from and out of contact with the nipple if the user so wishes.

Figure 3:
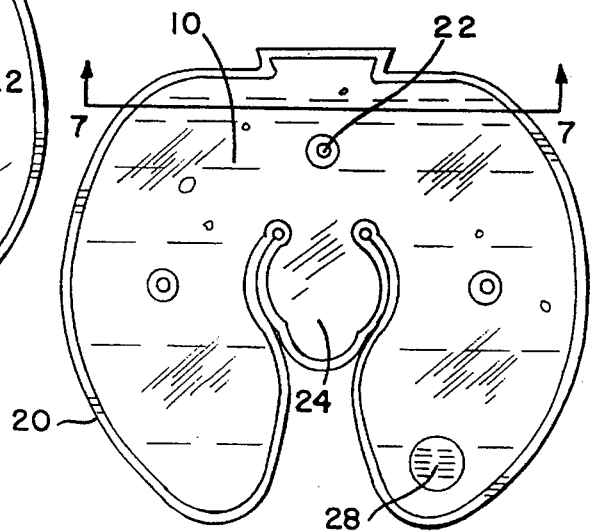
FIG. 3 is a top plan view of the embodiment of FIG. 2 after filling and removal of the fill spout.

FIG. 3 shows the device of FIG. 2 after the contents have been added and the edges completely sealed. In FIG. 2 the cavity 16 is empty. This empty cavity is filled with a chemical composition 26 that undergoes an exothermic reaction and a triggering device 28 that activates the exothermic reaction. After the cavity has been filled, the edge 20 is sealed again across the opening of the fill spout 18 as seen in the figures. This fully closes the heating pad 10, and the excess material of the fill spout 18 is removed by cutting or otherwise. This leaves the finished device as shown in FIG. 3.

The chemical composition 26 may be any chemical or mixture of chemicals that undergoes an exothermic reaction. Preferably the exothermic reaction is reversible. Also preferably the chemical composition 26 is a super-saturated solution of salt, such as a solution of sodium acetate or calcium nitrate tetrahydrate. Preferably it is a solution of sodium acetate of a concentration such that the exothermic reaction, when activated, achieves an internal temperature of about 98.6° to about 135° F. Most preferably, it is a solution of sodium acetate of a concentration such that the temperature achieved is about 110° to about 120° F.

The triggering device 28 is preferably a round metal disk with one or more slits in it. When flexed, the triggering device 28 initiates crystallization of the salt in solution. This crystallization evolves heat, the amount of heat varying with the concentration of the salt. A full description of the preferred triggering device 28 may be seen in U.S. Pat. Nos. 4,077,390 to Stanley et al., 4,572,158 to Fiedler, and 4,872, 442, 4,880,953, and 5,058,563 all to Manker, the entire disclosures of which are hereby incorporated by reference.

Figure 4:
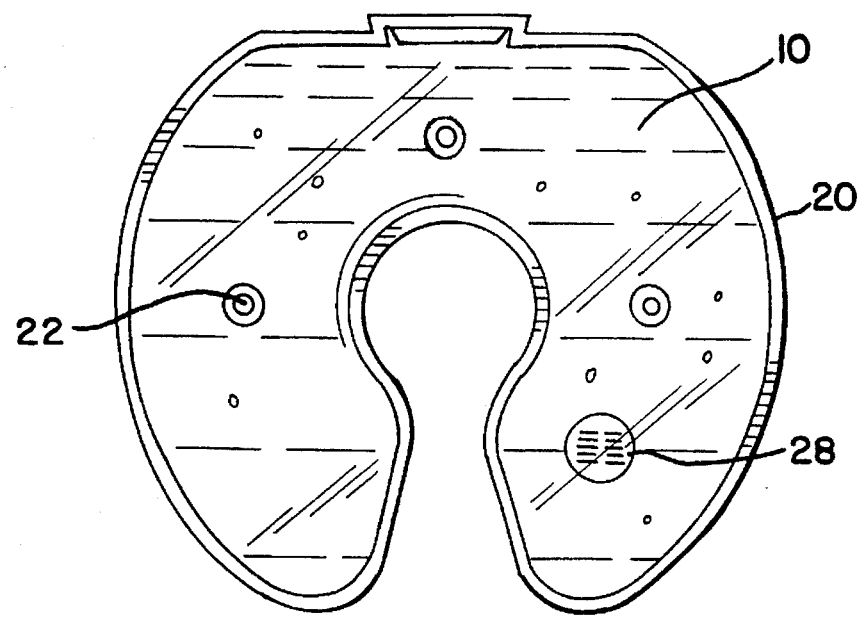
FIG. 4 is a top plan view of another embodiment of the invention.

FIG. 4 shows the same heating pad 10 as in FIG. 3, except that in this embodiment there is no nipple cover 24.

Figure 5:
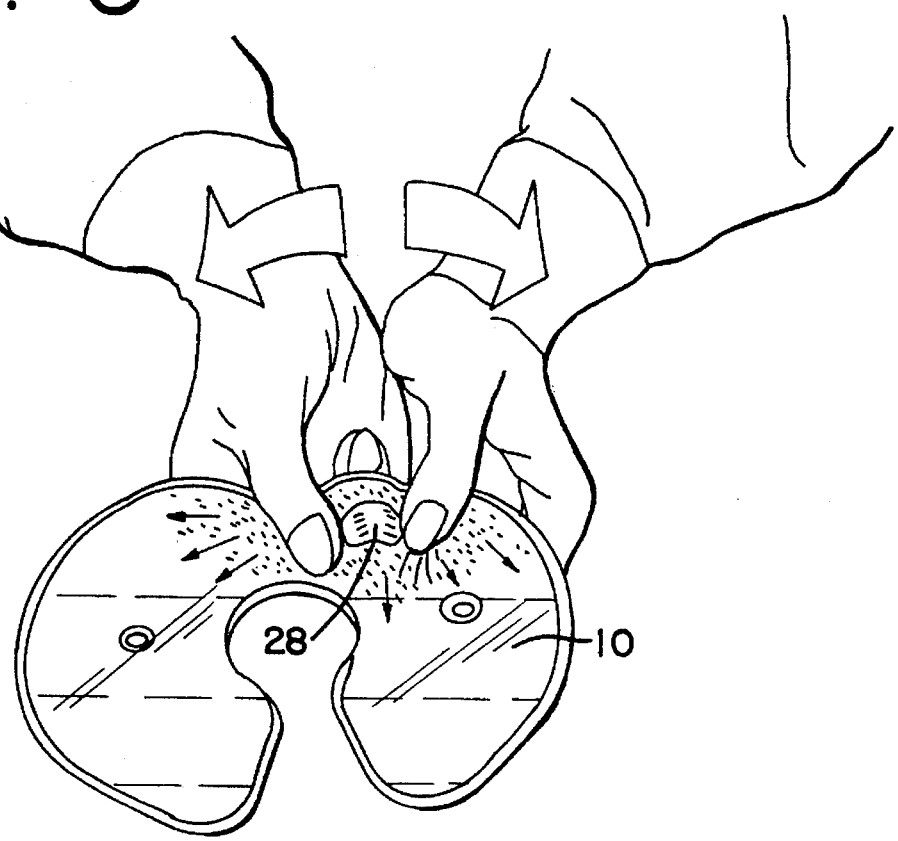
FIG. 5 is a perspective view of an embodiment of the invention showing how to activate the exothermic reaction.

FIG. 5 shows a person activating the chemical composition 26 by means of flexing the triggering device 28 as described above.

Figure 7:
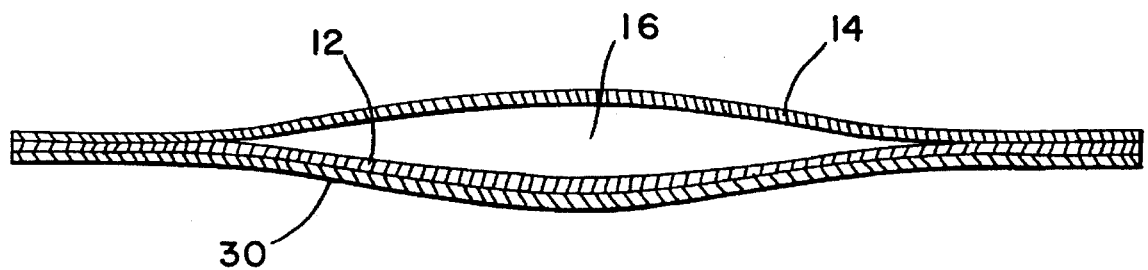
FIG. 7 is a cross sectional view of the heating pad taken along line 7—7 of FIG. 3.

In a further embodiment of the heating pad 10, as seen in FIG. 7, a layer of material 30 is added to the exterior of the front piece 12. This material 30 is meant to contact the breast 2 when the heating pad 10 is being used, and to thereby provide extra comfort to the user. The material 30 may be made of any type of cloth material such as polyester, cotton, nylon, rayon, silk, or other materials known to those skilled in the art. Most preferably it is composed of non-woven polyester.

Another feature may be added to increase user comfort. When sealing the edges of the front piece 12 and the back piece 14, the edge 20 is made to curve away from the front piece 12 and toward the back piece 14. Since it is intended that the front piece 12 directly engages the breast 2, this feature ensures that the edge 20, which may be rough, is pointed away from the user's skin.

Figure 6:
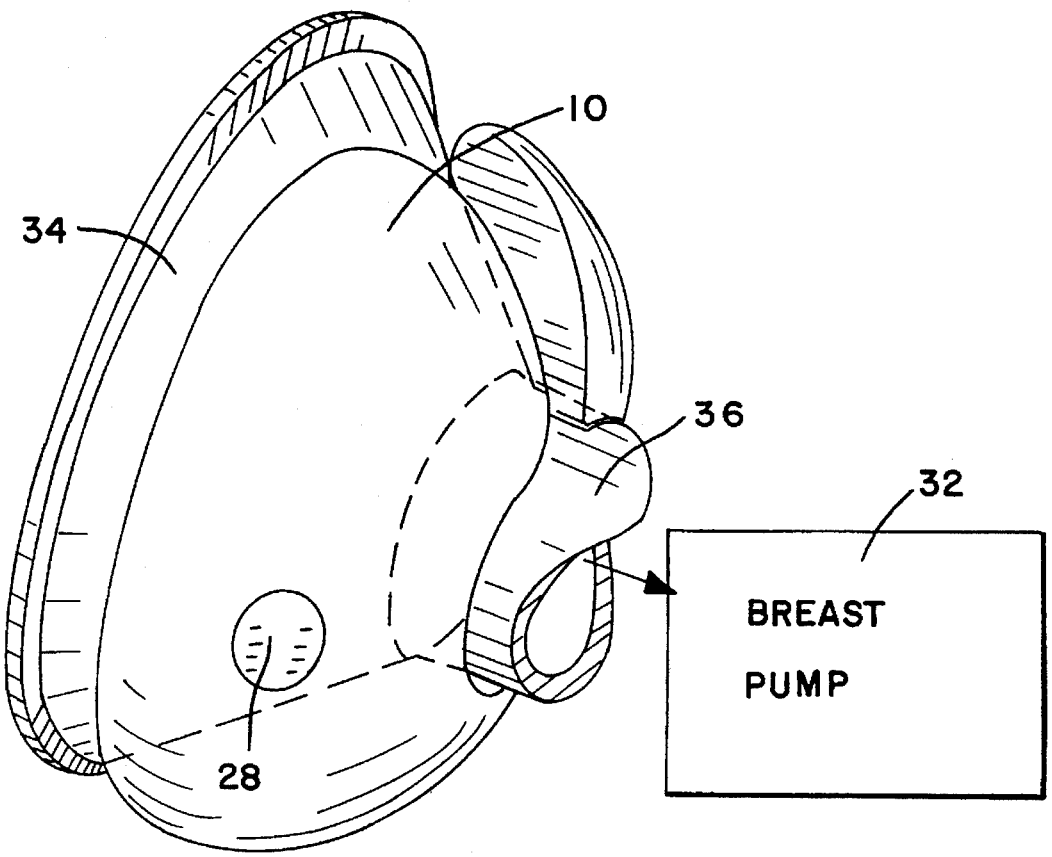
FIG. 6 is a perspective view of another embodiment of the invention, wherein the invention is shown connected to a breast pump.

Still another embodiment is shown in FIG. 6. This figure demonstrates the use of the heating pad 10 in conjunction with a breast pump 32. The breast pump 32 includes a breast shield 34. The breast shield 34 is a conically shaped part that does not include the apex of its cone. The breast shield 34 is placed over the breast 2 when in use, such that the nipple is located within the missing apex. In place of the apex of the cone of the breast shield 34 is a tube 36 that connects the breast shield 34 to the remainder of the breast pump 32. An exemplary breast pump that may be combined with the heating pad 10 of this invention to yield this embodiment is described in U.S. Pat. No. 4,929,229 to Larsson.

In this embodiment of the invention, a heating pad 10 is connected to the exterior of the breast shield 34. Since the breast shield 34 is in close physical contact with the breast 2 when in use, the heating pad 10 is only separated from the breast 2 by the thickness of the breast shield 34. Therefore, the heat generated by activating the heating pad 10 is conducted through the breast shield 34 and into the breast 2. Alternatively, the heating pad may be placed in the interior of the breast shield 34 or may be produced such that it is integral with the breast shield 34.

To insure that the proper amount of heat reaches the breast 2 through the insulating thickness of the breast shield 34, a higher concentration of salt is preferably used in the chemical composition 26 than in the other embodiments of the heating pad 10 described above. Most preferably the concentration of salt is such that a temperature of about 124° F. is achieved upon activation of the heating pad 10 in this embodiment.

In this embodiment the heating pad 10 may be connected to the breast shield 34 by any means known to the art, including heat sealing, ultrasonic welding and radio-frequency welding. More preferably, the heating pad 10 and the breast shield 34 are produced as one contiguous piece of material by blow molding, rotational molding, or other means known to those skilled in the art.

Further embodiments and improvements to this invention may be envisioned by those skilled in the art without departing from the spirit of this invention. All examples herein are intended to be descriptive and not limiting to the invention, which is defined herein only by the claims.

What is claimed is:

1. A heating pad adapted for use in warming the breast of a lactating woman, comprising:

a hollow, flattened, flexible, interrupted toroidal container, said container being sized to encompass a substantial portion of a woman's breast centered around the nipple, said flexibility provided to said container enabling said container to conform around a breast to which it is applied; and a chemical composition permanently sealed inside said container that undergoes an exothermic reaction when triggered, and that may be recharged after completion of the exothermic reaction for re-use of the pad in warming a breast.

2. The heating pad of claim 1 wherein the exothermic reaction is reversible and the heating pad is re-usable.

3. A heating pad comprising:

a hollow, flattened, interrupted toroidal container;

a chemical composition inside said container that undergoes an exothermic reaction when triggered, and that may be recharged after completion of the exothermic reaction; and a retractable nipple cover that is contiguous with said container and contains a portion of said chemical composition.

4. The heating pad of claim 1 wherein the chemical composition is a solution of sodium acetate.

5. The heating pad of claim 4 wherein the chemical composition comprises a concentration of sodium acetate sufficient to generate a temperature of about 98.6° to about 135° F. in response to being triggered.

6. The heating pad of claim 1 wherein the exothermic reaction is triggered by the flexing of a metal disk.

7. The heating pad of claim 1 wherein the heating pad achieves a temperature of about 98.6° to about 135° F. in response to being triggered.

8. The heating pad of claim 1 wherein the heating pad achieves a temperature of about 110° to about 120° F. in response to being triggered.

9. The heating pad of claim 1 wherein the container further comprises:

a front side that is adapted to contact a breast; and a back side that is peripherally connected to said front side so as to form said container.

10. The heating pad of claim 9 wherein the front side has a cloth surface that is adapted to contact the breast.

11. The heating pad of claim 9 wherein at least a portion of the front side or the back side is transparent.

12. The heating pad of claim 9 wherein the front side and the back side comprise plastic sheeting material.

13. The heating pad of claim 1 wherein the container has a flattened edge.

14. A method for making a heating pad comprising the steps of:

(a) providing a front piece comprising a water-proof material;

(b) sealing a back piece comprising a water-proof material to the front piece so as to form a C-shaped container;

(c) die-cutting the edges of the container;

(d) placing a chemical composition that is capable of undergoing an exothermic reaction inside the container; and (e) placing a triggering device that instigates the exothermic reaction inside the container.

15. The method of claim 14 wherein step (c) further comprises cutting the edges so that the edges are curved away from the front piece of the heating pad.

16. A heating pad comprising:

a C-shaped front piece comprising a water-proof material;

a C-shaped back piece comprising a water-proof material that is peripherally sealed to the front piece so as to form a container;

a chemical composition that is capable of undergoing an exothermic reaction, and that is present inside the container; and a triggering device inside the container that instigates the exothermic reaction.

\* \* \* \* \*